United States Patent [19]

Eicken et al.

[11] Patent Number: 4,567,263
[45] Date of Patent: Jan. 28, 1986

[54] 7-AMINOAZOLO[1,5-A]-PYRIMIDINES AND FUNGICIDES CONTAINING THESE COMPOUNDS

[75] Inventors: Karl Eicken, Wachenheim; Klaus Scheib, Schauernheim; Hans Theobald; Ernst-Heinrich Pommer, both of Limburgerhof; Eberhard Ammermann, Ludwigshafen, all of Fed. Rep. of Germany

[73] Assignee: BASF Aktiengesellschaft, Fed. Rep. of Germany

[21] Appl. No.: 651,660

[22] Filed: Sep. 18, 1984

Related U.S. Application Data

[63] Continuation of Ser. No. 401,346, Jul. 23, 1982, abandoned.

[30] Foreign Application Priority Data

Aug. 1, 1981 [DE] Fed. Rep. of Germany ....... 3130633

[51] Int. Cl.$^4$ ............................................. C07D 471/02
[52] U.S. Cl. ................................. 544/263; 260/465 R; 260/465 G; 260/465 F; 260/465 H; 544/281; 548/266; 548/373
[58] Field of Search ....................... 544/250, 263, 281; 424/251

[56] References Cited

U.S. PATENT DOCUMENTS

| | | | |
|---|---|---|---|
| 2,553,500 | 5/1951 | Harsh | 544/263 |
| 4,483,987 | 11/1984 | Wagner | 544/263 |

FOREIGN PATENT DOCUMENTS

| | | | |
|---|---|---|---|
| 2448542 | 9/1980 | France . | |
| 99794 | 8/1973 | German Democratic Rep. . | |
| 40-2679 | 2/1965 | Japan | 544/281 |
| 40-18757 | 8/1965 | Japan | 544/281 |
| 1148629 | 4/1969 | United Kingdom . | |

OTHER PUBLICATIONS

Eiden et al., *Arch. Pharm.* (Weinheim), 1971, vol. 304, No. 2, pp. 121–125.
Chemical Abstracts 63, 1804 f & g.
J. Pharm. Soc. Japan, vol. 84 (1964), pp. 1113–1118; Takamiza et al.
Chemical Week (1972) Jun. 21, p. 63.

*Primary Examiner*—Donald G. Daus
*Assistant Examiner*—Stephen M. Kapner
*Attorney, Agent, or Firm*—Keil & Weinkauf

[57] ABSTRACT

7-Aminoazolo[1,5-a]pyrimidine of the formula

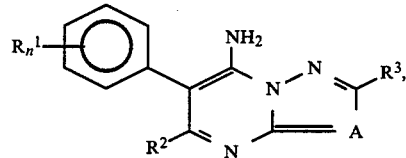

where $R^1$ is unsubstituted or substituted alkyl, halogen, alkoxy, cyano, or cycloalkyl, or is aryl, aryloxy, arylthio, arylalkyl, arylalkoxy or arylalkylthio, each of which may be substituted, or is indane, tetrahydronaphthalene or benzene, each of which may be substituted and is fused to the phenyl ring, $R^2$ and $R^3$ are each hydrogen, alkyl or aryl, n is 1 or 2, A is nitrogen or a $CR^4$ group, where $R^4$ has the meanings of $R^2$ and may furthermore be halogen, cyano or alkoxycarbonyl, or together with $R^3$ is alkylene which may have up to 2 double bonds, and fungicides containing these compounds.

8 Claims, No Drawings

7-AMINOAZOLO[1,5-A]-PYRIMIDINES AND FUNGICIDES CONTAINING THESE COMPOUNDS

This application is a continuation of application Ser. No. 401,346, filed on July 23, 1982 now abandoned.

The present invention relates to novel 7-aminoazolo[1,5-a]pyrimidines, a process for their preparation, and fungicides containing these compounds.

It has been disclosed that 7-aminoazolo[1,5-a]pyrimidines, eg. 7-amino-2-methyl-5-phenylpyrazolo[1,5-a]pyrimidine, possess pharmacological properties (French Pat. No. 2,448,542; East German Pat. Nos. 99,794 and 55,956; and J. Pharm. Soc. Japan 84 (1964), 1113-1118). It has also been disclosed that N-trichloromethylthiophthalimide can be used as a fungicide (Chemical Week 1972, 21st June, page 63).

We have found that novel 7-aminoazolo[1,5-a]pyrimidines of the formula

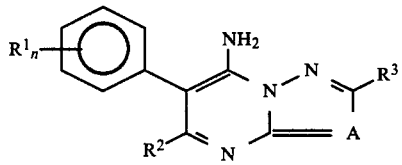

where $R^1$ is unsubstituted, halogen-substituted or alkoxy-substituted alkyl, halogen, alkoxy, cyano, or cycloalkyl, or is aryl, aryloxy, arylthio, arylalkyl, arylalkoxy or arylalkylthio, each of which may be substituted by alkyl, alkoxy, halogen or cyano, or is benzene, indane or tetrahydronaphthalene, each of which may be substituted by alkyl, alkoxy, halogen or cyano, and each of which is fused to the phenyl ring, n is 1 or 2, $R^2$ and $R^3$ are each hydrogen, alkyl or aryl, and A is nitrogen or a $CR^4$ group, where $R^4$ has the meanings of $R^2$ and halogen, cyano or alkoxycarbonyl, or together with $R^3$ is alkylene which may have up to two double bonds, exhibit a good fungicidal action, in particular against Phycomycetes.

$R^1$ is, for example, $C_1-C_{12}$-alkyl which is unsubstituted or substituted by fluorine, chlorine, bromine or $C_1-C_4$-alkoxy, or is fluorine, chlorine, bromine, $C_1-C_{12}$-alkoxy, cyano, or $C_3-C_8$-cycloalkyl, or is aryl (phenyl), aryloxy (phenoxy), arylthio (phenylthio), arylalkyl (benzyl), arylalkoxy (benzoxy), arylalkylthio (benzylthio) where alkyl is of 1 to 6 carbon atoms, each of which may be substituted by $C_1-C_4$-alkyl, $C_1-C_4$-alkoxy, cyano, fluorine, chlorine or bromine, or is indane, tetrahydronaphthalene or benzene, each of which may be substituted by $C_1-C_4$-alkyl, $C_1-C_4$-alkoxy, cyano, fluorine or bromine, and each of which is fused to the phenyl ring.

$R^2$ and $R^3$, and $R^4$ where this has the meanings of $R^2$, are, for example, hydrogen or $C_1-C_4$-alkyl, or phenyl which is unsubstituted or substituted by chlorine, $C_1-C_4$-alkyl or $C_1-C_4$-alkoxy. $R^4$ may furthermore be chlorine, bromine, cyano or $C_1-C_4$-alkoxycarbonyl, or together with $R^3$ may be $C_3-C_4$-alkylene which may contain one or two double bonds. Alkyl or the alkyl radical of an alkoxy group in the radicals $R^1$, $R^2$, $R^3$ and $R^4$ is, depending on the stated number of carbon atoms, methyl, ethyl, propyl, butyl, pentyl, hexyl, heptyl, octyl, nonyl, decyl, undecyl or dodecyl, or an isomer thereof.

We have also found that 7-aminoazolo[1,5-a]pyrimidines of the formula I are obtained when a substituted benzyl cyanide of the formula

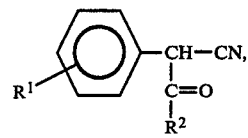

where $R^1$ and $R^2$ have the above meanings, is reacted with a 5(3)-aminopyrazole of the formula

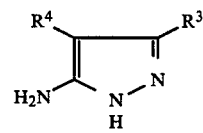

or with a 5(3)-amino-1,2,4-triazole of the formula

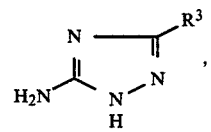

where $R^3$ and $R^4$ have the above meanings.

The reaction can be carried out in the presence or absence of a solvent. It is advantageous to use a solvent which is inert to the starting materials, and in which some or all of the latter are soluble. Particularly suitable solvents are alcohols, eg. ethanol, propanols, butanols, glycols and glycol monoethers, and diethylene glycols and their monoethers, amides, eg. dimethylformamide, diethylformamide, dibutylformamide and N,N-dimethylacetamide, lower alkanoic acids, eg. formic acid, acetic acid and propionic acid, and mixtures of these solvents with water. In solution, the reaction is carried out at from 50° to 300° C., preferably from 50° to 150° C.

The novel 7-aminoazolo[1,5-a]pyrimidines are isolated, if necessary after evaporating the solvent or diluting the solution with water, as crystalline compounds, which are very pure in most cases. When a lower alkanoic acid is used as the solvent, it is advantageous, after evaporating some of the alkanoic acid if necessary, to neutralize the residual alkanoic acid by the addition of an aqueous alkali, the novel 7-aminoazolo[1,5-a]pyrimidine crystallizing out in very pure form in most cases.

Some of the substituted benzyl cyanides of the formula

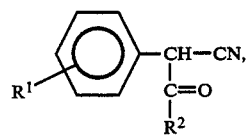

which are required for the preparation of the 7-aminoazolo[1,5-a]pyrimidines are known, and others may be prepared from benzyl cyanides and carboxylates with alkali metal alcoholates or alkali metal hydrides, using conventional methods (J. Amer. Chem. Soc. 73 (1951), 3766).

General method for the preparation of the substituted benzyl cyanide of the formula II:

1.5 moles of a sodium alcoholate are introduced into 1 l of toluene, and 1.0 mole of a benzyl cyanide followed by 2.0 moles of a carboxylate are added dropwise, while stirring, the temperature increasing to 40°–50° C. Stirring is continued for 2 hours at 75°–80° C., after which the mixture is cooled and 2 l of water are added. The aqueous phase is washed twice with 0.2 l of toluene, after which it is acidified to pH 2 with half-concentrated (about 50% strength by weight) sulfuric acid to give the substituted benzyl cyanide of the formula II (yield: from 70 to 90%).

The following substituted benzyl cyanides of the formula

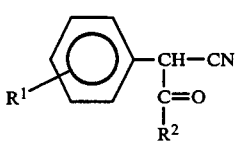

II can be prepared in this manner:

| $R^1$ | $R^2$ | Mp. (°C.) |
| --- | --- | --- |
| 2-CH$_3$ | H | 89 |
| 3-CH$_3$ | H | 119 |
| 4-C(CH$_3$)$_3$ | H | 169 |
| 3-CH$_3$O | H | 102 |
| 3-Cl | H | 178 |
| 4-Cl | H | 164 |
| 4-Br | H | 176 |
| 3-CF$_3$ | H | 107 |
| 3-CF$_3$ | CH$_3$ | 82 |
| 3-C$_6$H$_5$O | H | 45 |
| 4-C$_2$H$_5$ | H | 90 |
| 4-C$_6$H$_{13}$O | H | 116 |
| 4-iC$_3$H$_7$ | H | 84 |
| (3)(4) fused ring | H | 205 |
| 3,4-Cl$_2$ | H | 170 |
| 2-CH$_3$, 4-C(CH$_3$)$_3$ | H | 120 |
| 4-C$_6$H$_5$ | H | 228 |
| 4-C$_6$H$_5$CH$_2$—O | H | 188 |
| 4 (ClCH$_2$CH(CH$_3$)CH$_2$) | H | Oil |
| 2,4-Cl | H | 166 |
| 4-CN | H | 222 |
| $R^1$ = β-naphthyl | H | |
| $R^1$ = α-naphthyl | H | |

The Examples which follow illustrate the preparation of the novel active ingredients.

EXAMPLE 1

21.3 g of m-trifluoromethyl-2-formylbenzyl cyanide and 9.7 g of 3(5)-amino-5(3)-methylpyrazole in 100 ml of glacial acetic acid were refluxed for 4 hours. The mixture was cooled and was then diluted with 500 ml of water, the pH was brought to 5–6 with 2N NaOH solution, and the oily product which precipitated crystallized after trituration. The crystals were filtered off under suction and then washed several times with water and dried under reduced pressure at 50° C. 25.0 g of 7-amino-2-methyl-6-(3'-trifluoromethylphenyl)-pyrazolo[1,5-a]pyrimidine of melting point 176° C. were obtained (Compound 10).

$C_{14}H_{11}N_4F_3$ (M 292). Calculated: C 57.54, H 3.79, N 19.17. Found: C 57.6, H 3.9, N 18.9.

EXAMPLE 2

10.5 g of p-tert.-butyl-2-formylbenzyl cyanide and 4.8 g of 3(5)-amino-5(3)-methylpyrazole in 40 ml of dimethylformamide were refluxed for 3 hours. The mixture was cooled, and 150 ml of water were then added dropwise. The crystals were filtered off under suction and then washed with water and dried under reduced pressure at 50° C. 11.3 g of 7-amino-2-methyl-6-(4'-tert.-butylphenyl)-pyrazolo[1,5-a]pyrimidine of melting point 218° C. were obtained (Compound 5).

$C_{17}H_{20}N_4$ (M 280). Calculated: C 72.83, H 7.19, N 19.98. Found: C 72.8, H 7.1, N 19.9.

EXAMPLE 3

11.8 g of m-phenoxy-2-formylbenzyl cyanide and 4.3 g of 3-aminotriazole in 40 ml of glacial acetic acid were refluxed for 6 hours, the mixture was cooled, 300 ml of water were then added, and the pH was brought to 6 with 2N NaOH. The precipitated crystals were filtered off under suction and dried (14.1 g). This material was dissolved in 30 ml of hot dimethylformamide, the solution was cooled, the product was precipitated with 10 ml of methanol, and the crystals were filtered off under suction, washed with a further amount of methanol and dried. 9.6 g of 7-amino-6-(3'-phenoxyphenyl)-1,2,4-triazolo[1,5-a]pyrimidine of melting point 248°–250° C. were obtained (Compound 44).

$C_{17}H_{13}N_5O$ (M 303). Calculated: C 67.32, H 4.32, N 23.09. Found: C 67.8, H 4.2, N 22.9.

The following 7-aminoazolo[1,5-a]pyrimidines were prepared by the process described above.

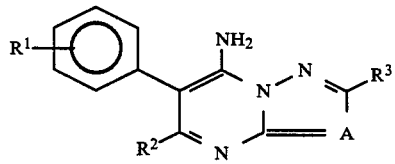

| No. | $R^1$ | $R^2$ | $R^3$ | $R^4$ | A | M.p. (°C.) |
| --- | --- | --- | --- | --- | --- | --- |
| 1 | 3-CF$_3$ | CH$_3$ | CH$_3$ | H | CR$^4$ | 212 |
| 2 | 3,4(CH$_3$O)$_2$ | CH$_3$ | CH$_3$ | H | CR$^4$ | 188 |

-continued

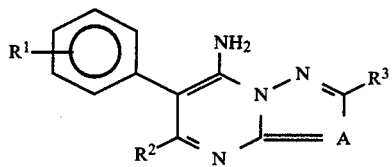

| No. | R¹ | R² | R³ | R⁴ | A | M.p. (°C.) |
|---|---|---|---|---|---|---|
| 3 | 2-CH₃ | H | CH₃ | H | CR⁴ | 224 |
| 4 | 3-CH₃ | H | CH₃ | H | CR⁴ | 158 |
| 5 | 4-C(CH₃)₃ | H | CH₃ | H | CR⁴ | 218 |
| 6 | 3-CH₃O | H | CH₃ | H | CR⁴ | 124 |
| 7 | 3-Cl | H | CH₃ | H | CR⁴ | 174 |
| 8 | 4-Cl | H | CH₃ | H | CR⁴ | 168 |
| 9 | 4-Br | H | CH₃ | H | CR⁴ | 171 |
| 10 | 3-CF₃ | H | CH₃ | H | CR⁴ | 176 |
| 11 | 3-C₆H₅O | H | CH₃ | H | CR⁴ | 173 |
| 12 | 4-C₂H₅ | H | CH₃ | H | CR⁴ | 150 |
| 13 | 4-H₁₃C₆O | H | CH₃ | H | CR⁴ | 132 |
| 14 | (benzyl (3),(4)) | H | CH₃ | H | CR⁴ | 328 |
| 15 | 4-iC₃H₇ | H | CH₃ | H | CR⁴ | 162 |
| 16 | 3,4-Cl₂ | H | CH₃ | H | CR⁴ | 160 |
| 17 | 4-C(CH₃)₃; 2-CH₃ | H | CH₃ | H | CR⁴ | 238 |
| 18 | 4-C₆H₅ | H | CH₃ | H | CR⁴ | 197 |
| 19 | 4-C₆H₅—CH₂O | H | CH₃ | H | CR⁴ | 160 |
| 20 | 4-(ClCH₂CH(CH₃)CH₂) | H | CH₃ | H | CR⁴ | 168 |
| 21 | 2,4-Cl₂ | H | CH₃ | H | CR⁴ | 245 |
| 22 | 3-CF₃ | H | H | C₆H₅ | CR⁴ | 184 |
| 23 | 3-CF₃ | H | CH=CH—CH=CH | | CR⁴ | 243 |
| 24 | 4-C(CH₃)₃ | H | CH=CH—CH=CH | | CR⁴ | 248 |
| 25 | 4-CH₃O | CH₃ | CH₃ | H | CR⁴ | 200 |
| 26 | 3-C₆H₅O | H | H | H | CR⁴ | 166 |
| 27 | 4-C(CH₃)₃ | H | H | H | CR⁴ | 210 |
| 28 | 3-CF₃ | CH₃ | H | CO₂CH₃ | CR⁴ | 273 |
| 29 | 3-CF₃ | CH₃ | H | CO₂C₂H₅ | CR⁴ | 196 |
| 30 | 4-C(CH₃)₃ | H | H | C₆H₅ | CR⁴ | 231 |
| 31 | 4-CN | H | CH₃ | H | CR⁴ | 229 |
| 32 | 4-C(CH₃)₃ | H | CH₃ | Br | CR⁴ | 258 |
| 34 | R¹–⟨⟩– = β-Naphthyl | H | CH₃ | H | CR⁴ | 242 |
| 35 | R¹–⟨⟩– = α-Naphthyl | H | CH₃ | H | CR⁴ | 211 |
| 36 | 2-CH₃ | H | H | — | N | 252 |
| 37 | 3-CH₃ | H | H | — | N | 222 |
| 38 | 3-CH₃O | H | H | — | N | 246 |
| 39 | 3-CF₃ | H | H | — | N | 280 |
| 41 | 4-C(CH₃)₃ | H | H | — | N | 327 |
| 42 | 3-Cl | H | H | — | N | 282 |
| 43 | 4-Br | H | H | — | N | 303 |
| 44 | 3-C₆H₅O | H | H | — | N | 250 |
| 45 | 4-Cl | H | H | — | N | 257 |
| 46 | 4-C₂H₅ | H | H | — | N | 268 |
| 47 | 4-C(CH₃)₃; 2-CH₃ | H | H | — | N | 288 |
| 48 | 4-C₆H₅ | H | H | — | N | 300 |
| 49 | 4-H₁₃C₆—O | H | H | — | N | 256 |
| 50 | 4-i-C₃H₇ | H | H | — | N | 272 |
| 51 | 3,4-Cl₂ | H | H | — | N | 284 |
| 52 | 2,4-Cl₂ | H | H | — | N | 283 |
| 53 | 4(ClCH₂CH(CH₃)CH₂) | H | H | — | N | 217 |
| 54 | 4-C₆H₅CH₂—O | H | H | — | N | 268 |
| 55 | 4-CN | H | H | — | N | 345 |
| 57 | 4-C(CH₃)₃ | H | C₆H₅ | — | N | 370 |
| 58 | 4-C(CH₃)₃ | CH₃ | CH₃ | H | CR⁴ | 242 |
| 59 | 4-C(CH₃)₃ | C₂H₅ | CH₃ | H | CR⁴ | 168 |
| 60 | 4-C(CH₃)₃ | n-C₃H₇ | CH₃ | H | CR⁴ | 192 |
| 61 | 4(4'-C(CH₃)₃—C₆H₄CH₂O) | H | CH₃ | H | CR⁴ | 207 |
| 62 | 4-C(CH₃)₃ | H | CH₃ | CN | CR⁴ | 300 |

-continued

| No. | R¹ | R² | R³ | R⁴ | A | M.p. (°C.) |
|---|---|---|---|---|---|---|
| 63 | R¹—⬡⬡ = beta-Naphthyl | H | H | — | N | 201 |
| 64 | 4-cycl.C$_6$H$_{11}$ | H | CH$_3$ | H | CR$^4$ | 200 |
| 65 | 4-C(CH$_3$)$_3$ | CH$_3$ | CH$_3$ | Br | CR$^4$ | 260 |
| 66 | 4-C$_2$H$_5$O | CH$_3$ | CH$_3$ | H | CR$^4$ | 218 |
| 67 | 4-C$_2$H$_5$O | H | H | — | N | 258 |
| 68 | 4-C$_2$H$_5$O | H | CH$_3$ | H | CR$^4$ | 185 |
| 69 | 4-C$_2$H$_5$O | CH$_3$ | H | — | N | 202 |
| 70 | 4-nH$_{13}$C$_6$O | CH$_3$ | CH$_3$ | H | CR$^4$ | 168 |
| 71 | 4(CH$_2$=CH—CH$_2$O) | H | H | — | N | 235 |
| 72 | 4(CH$_2$=CH—CH$_2$O) | H | CH$_3$ | H | CR$^4$ | 161 |
| 73 | 4(n-C$_4$H$_9$—CH(C$_2$H$_5$)—CH$_2$O) | H | CH$_3$ | H | CR$^4$ | 102 |
| 74 | 4(n-C$_4$H$_9$—CH(C$_2$H$_5$)—CH$_2$O) | H | H | — | N | 199 |
| 75 | 4(n-C$_{12}$H$_{25}$O) | H | CH$_3$ | H | CR$^4$ | 98 |
| 76 | 4(n-C$_{12}$H$_{25}$O) | H | H | — | N | 198 |
| 77 | 4(n-C$_4$H$_9$O) | H | CH$_3$ | H | CR$^4$ | 181 |
| 78 | 4(n-C$_4$H$_9$O) | H | H | — | N | 235 |
| 79 | 4(i-C$_4$H$_9$O) | H | CH$_3$ | H | CR$^4$ | 211 |
| 80 | 4(i-C$_4$H$_9$O) | H | H | — | N | 270 |

The following compounds may be prepared analogously:

| No. | R¹ | R² | R³ | R⁴ | A | M.p.(°C.) |
|---|---|---|---|---|---|---|
| 33 | 4-C(CH$_3$)$_3$ | H | —(CH$_2$)$_3$— | | — | |
| 40 | 3-CF$_3$ | CH$_3$ | H | | N | |
| 56 | 4-C(CH$_3$)$_3$ | CH$_3$ | H | | — | |

The novel active ingredients have a strong fungitoxic action on phytopathogenic fungi, especially from the Phycomycetes class. The novel compounds are therefore suitable for instance for combating *Phytophthora infestans* in tomatoes and potatoes, *Phytophthora parasitica* in strawberries, *Phytophthora cactorum* in apples, *Pseudoperonospora cubensis* in cucumbers, *Pseudoperonospora humuli* in hops, *Peronospora destructor* in onions, *Peronospora sparsa* in roses, *Peronospora tabacina* in tobacco, *Plasmopara viticola* in grapes, *Plasmopara halstedii* in sunflowers, *Sclerospora macrospora* in Indian corn, *Bremia lactucae* in lettuce, *Mucor mucedo* in fruit, *Rhizopus nigricans* in beets, *Erysiphe graminis* in cereals, *Uncinula necator* in grapes, *Podosphaera leucotricha* in apples, *Sphaerotheca fuliginea* in roses, and *Erysiphe cichoriacearum* in cucumbers. The fungicidal agents contain from 0.1 to 95, and preferably from 0.5 to 90, wt% of active ingredient. The application rates depend on the type of effect desired, and range from 0.1 to 5 kg of active ingredient per hectare.

The agents according to the invention may also be mixed and applied with other active ingredients, e.g., herbicides, insecticides, growth regulators, fungicides and fertilizers. When mixed with other fungicides, the spectrum of fungicidal action is in many cases increased; with a number of these fungicidal compositions, synergistic effects also occur; i.e., the fungicidal action of the combination product is greater than the effect of the individual components added together. The spectrum of action is particularly favorably influenced when the compounds according to the invention are mixed with the following fungicides:

manganese N,N-ethylene-bis-dithiocarbamate, manganese zinc N,N-ethylenediamine-bis-dithiocarbamate, the ammonia complex of zinc N,N-ethylene-bis-dithiocarbamate and N,N'-polyethylene-bis-(thiocarbamoyl)-disulfide, N-trichloromethylthiotetrahydrophthalimide, N-trichloromethylthio-phthalimide, 5-ethoxy-3-trichloromethyl-1,2,3-thiadiazole, 2-methoxycarbonylaminobenzimidazole, 2-thiocyanomethylthiobenzothiazole, 1,4-dichloro-2,5-dimethoxybenzene, 2,3-dichloro-6-methyl-1,4-oxathiin-5-carboxylic acid anilide, 2-methyl-5,6-dihydro-4H-pyran-3-carboxylic acid anilide, 2,4,5-trimethylfuran-3-carboxylic acid anilide, 2-methylfuran-3-carboxylic acid anilide, 2,5-dimethylfuran-3-carboxylic acid cyclohexylamide, N-cyclohexyl-N-methoxy-2,5-dimethylfuran-3-carboxylic acid amide, 5-methyl-5-vinyl-3-(3,5-dichlorophenyl)-2,4-dioxo-1,3-oxazolidine, and 3-(3,5-dichlorophenyl)-5-methyl-5-methoxymethyl)-1,3-oxazolidine-2,4-dione.

The following list of fungicidal active ingredients with which the compounds according to the invention may be combined is intended to illustrate and not to restrict the combination possibilities. Examples are as follows:

dithiocarbamates and their derivatives, e.g. iron(III) dimethyldithiocarbamate, zinc dimethyldithiocarbamate, zinc N,N-ethylene-bis-dithiocarbamate, tetramethylthiuram disulfide, zinc N,N-propylene-bis-dithiocarbamate, and the ammonia complex of zinc N,N-propylene-bis-dithiocarbamate and N,N'-polypropylene-bis-(thiocarbamoyl)-disulfide, nitro derivatives, e.g. dinitro-(1-methylheptyl)-phenyl crotonate, 2-sec.-butyl-4,6-dinitrophenyl, 3,3-dimethylacrylate and 2-sec.-butyl-4,6-dinitrophenyl isopropyl carbonate; heterocyclic compounds, e.g. 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 2,3-dicyano-1,4-dithioanthraquinone, 2-thio-1,3-dithio-(4,5-b)-quinoxaline, methyl 1-(butylcarbamoyl)-2-benzimidazole-carbamate, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenylsulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, alpha-(2-chloro-phenyl-alpha-(4-chlorophenyl)-5-pyrimidine-methanol, and 1-(4-chlorophenoxy)-3,3-dimethyl-1-(1H-1,2,4-triazol-1-yl)-2-butanone, and 1-(4-chlorophenoxy)-3,3-dimethyl-1-(1H-1,2,4-triazol-1-yl)-2-butanol.

The novel active ingredients are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

For the experiment described below, the following prior art compounds were used for comparison purposes:

N-trichloromethylthiophthalimide (compound A)
7-amino-2-methyl-5-phenylpyrazolo[1,5-a]-pyrimidine (compound B).

EXPERIMENT 1

Action on *Plasmopara viticola*

Leaves of potted vines of the Müller-Thurgau variety were sprayed with aqueous suspensions containing (dry basis) 80% (wt%) of active ingredient and 20% of emulsifier. To assess the duration of action, the plants were set up, after the sprayed-on layer had dried, for 10 days in the greenhouse. Then the leaves were infected with a zoospore suspension of *Plasmopara viticola*. The plants were first placed for 16 hours in a steam-saturated (moist) chamber at 24° C., and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

In this test, for example active ingredients nos. 1, 5, 10, 11, 12, 13, 15, 16, 17, 18, 19, 20, 27, 37, 41, 42 and 44, applied as a 0.025% spray, had a better fungicidal action (e.g., 100%) than the prior art comparative compounds A and B (e.g., 60%).

Examples of formulations are given below.

I. 90 parts by weight of compound 1 is mixed with 10 parts by weight of N-methyl-alpha-pyrrolidone. A mixture is obtained which is suitable for application in the form of very fine drops.

II. 20 parts by weight of compound 5 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound 10 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound 11 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound 37 is well mixed with 3 parts by weight of the sodium salt of diisobutyl-naphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound 41 is intimately mixed with 97 parts by weight of particulate kaolin. A dust is obtained containing 3% by weight of the active ingredient.

VII. 30 parts by weight of compound 42 is intimately mixed with a mixture consisting of 92 parts by weight of powdereed silica gel and 8 parts by weight of paraffin oil which has been sprayed onto the surface of this silica gel. A formulation of the active ingredient is obtained having good adherence.

VIII. 40 parts by weight of compound 44 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A 7-amminoazolo[1,5-a]pyrimidine of the formula

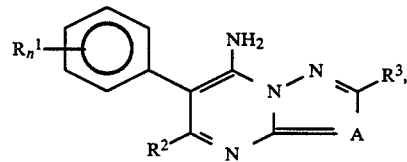

I where $R^1$ is unsubstituted alkyl of 1-12 carbons, halogen-substituted or alkoxy of 1-4 carbons-substituted alkyl of 1-12 carbons, halogen, alkoxy of 1-12 carbons, cyano, or cycloalkyl, or is phenyloxy, phenylthio, phenylalkyl, phenylalkoxy or phenylalkylthio wherein the alkyl is 1-6 carbons, each of which may be substituted by alkyl of 1-4 carbons, alkoxy of 1-4 carbons, halogen or cyano or is phenyl which is substituted by alkyl of 1-4 carbons, alkoxy of 1-4 carbons, halogen or cyano or is indane which may be substituted by alkyl of 1-4 carbons, alkoxy of 1-4 carbons, halogen or cyano and each of which is fused to the phenyl ring n is 1 or n is 2 when two substituents are in the 2,4- and 3,4 positions, $R^2$ and $R^3$ are each hydrogen, alkyl of 1-4 carbons or phenyl, and A is nitrogen or a $CR^4$ group, where $R^4$ has the meanings of $R^2$ and halogen, cyano or alkoxycarbonyl, or together with $R^3$ is alkylene which may have up to two double bonds.

2. A compound of the formula I as set forth in claim 1, wherein n is 1.

3. A compound of the formula I as set forth in claim 2, wherein $R^2$ and $R^3$ are each hydrogen, alkyl of 1-4 carbons or phenyl.

4. A 7-aminoazolo[1,5-a]pyrimidine as defined in claim 1, wherein $R^1$ is $CF_3$, t-butyl, ethoxy or phenoxy; $R^2$ is hydrogen; $R^3$ is hydrogen or $CH_3$ and n is 1.

5. A 7-aminoazolo[1,5-a]pyrimidine as defined in claim 1, where $R^2$ is hydrogen or methyl, $R^3$ is hydrogen or methyl, and $R^4$ is hydrogen.

6. A process for combating fungi, wherein the fungi or the objects to be protected against fungus attack are treated with a 7-aminoazolo[1,5-a]pyrimidine of the formula

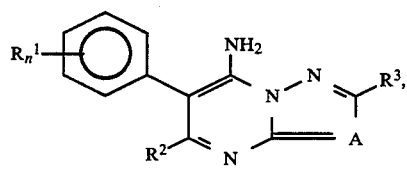

I where $R^1$ is unsubstituted alkyl of 1-12 carbons, halogen-substituted or alkoxy of 1-4 carbons-substituted alkyl of 1-12 carbons, halogen, alkoxy of 1-12 carbons, cyano, or cycloalkyl, or is phenyl, phenyloxy, phenylthio, phenylalkyl, phenylalkoxy or phenylalkylthio wherein the alkyl is 1-6 carbons, each of which may be substituted by alkyl of 1-4 carbons, alkoxy of 1-4 carbons, halogen or cyano, or is indane, or benzene, each of which may be substituted by alkyl of 1-4 carbons, alkoxy of 1-4 carbons, halogen or cyano and each of which is fused to the phenyl ring, n is 1 or 2, $R^2$ and $R^3$ are each hydrogen, alkyl of 1-4 carbons or phenyl, and A is nitrogen or a $CR^4$ group, where $R^4$ has the meanings of $R^2$ and halogen, cyano or alkoxycarbonyl, or together with $R^3$ is alkylene which may have up to two double bonds.

7. A process for combating fungi as set out in claim 6, wherein $R^1$ is unsubstituted alkyl of 1-12 carbons or alkyl of 1-12 carbons substituted by alkyl of 1-4 carbons, halogen or alkoxy of 1-4 carbons.

8. A process for combating fungi as set out in claim 6, wherein $R^1$ is $CF_3$, t-butyl, ethoxy or phenoxy; $R^2$ is hydrogen; $R^3$ is hydrogen or $CH_3$ and n is 1.

* * * * *

UNITED STATES PATENT AND TRADEMARK OFFICE
CERTIFICATE OF CORRECTION

PATENT NO. : 4,567,263
DATED : January 28, 1986
INVENTOR(S) : Karl EICKEN et al.

It is certified that error appears in the above—identified patent and that said Letters Patent is hereby corrected as shown below:

IN THE CLAIMS:

Claim 1, column 11, line 68, change "amminoazolo"

to --aminoazolo--.

Signed and Sealed this

Twenty-ninth Day of April 1986

[SEAL]

Attest:

DONALD J. QUIGG

Attesting Officer     Commissioner of Patents and Trademarks